(12) United States Patent
Bermann et al.

(10) Patent No.: US 8,841,489 B2
(45) Date of Patent: Sep. 23, 2014

(54) METHOD FOR CARRYING OUT MULTIPHASE ALDOL CONDENSATION REACTIONS TO GIVE MIXED α,β-UNSATURATED ALDEHYDES

(75) Inventors: Dirk Bermann, Mülheim (DE); Guido D. Frey, Riedstadt (DE); Norman Nowotny, Essen (DE); Kurt Schalapski, Oberhausen (DE); Heinz Strutz, Moers (DE)

(73) Assignee: Oxea GmbH, Oberhausen (DE)

( * ) Notice: Subject to any disclaimer, the term of this patent is extended or adjusted under 35 U.S.C. 154(b) by 0 days.

(21) Appl. No.: 13/989,455

(22) PCT Filed: Feb. 9, 2012

(86) PCT No.: PCT/EP2012/000523
§ 371 (c)(1),
(2), (4) Date: Sep. 12, 2013

(87) PCT Pub. No.: WO2012/116775
PCT Pub. Date: Sep. 7, 2012

(65) Prior Publication Data
US 2014/0005441 A1    Jan. 2, 2014

(30) Foreign Application Priority Data

Mar. 3, 2011 (DE) .......... 10 2011 012 846

(51) Int. Cl.
C07C 45/72    (2006.01)
C07C 45/74    (2006.01)
C07C 45/45    (2006.01)

(52) U.S. Cl.
CPC ............ C07C 45/45 (2013.01); C07C 45/74 (2013.01)
USPC ............ 568/461; 568/463; 568/464

(58) Field of Classification Search
CPC ............... C07C 45/72; C07C 45/74
USPC ........................... 568/461, 463, 464
See application file for complete search history.

(56) References Cited

U.S. PATENT DOCUMENTS

| | | |
|---|---|---|
| 2,468,710 A | 4/1949 | Hull |
| 3,763,247 A | 10/1973 | Lemke et al. |
| 6,340,778 B1 * | 1/2002 | Bueschken et al. ........... 568/463 |

FOREIGN PATENT DOCUMENTS

| | | |
|---|---|---|
| DE | 927626 C | 5/1955 |
| DE | 102009001594 A1 | 9/2010 |
| EP | 0420035 A1 | 4/1991 |
| EP | 1106596 A2 | 6/2001 |
| GB | 761203 A | 11/1956 |
| WO | 2010105892 A1 | 9/2010 |

OTHER PUBLICATIONS

International Search Report dated Aug. 22, 2012.
Dr. G. Dümbgen et al., Großtechnische Herstellung von Oxo—Alkoholen aus Propylen in der BASF, Chemie-Ing.-Techn., (1969), pp. 974-980, 41, No. 17.
F.A. Streiff et al., New Fundamentals for Liquid—Liquid Dispersion Using Static Mixers, Récents Progrès en Génie des Procédés (1997) pp. 307-314, vol. 11, No. 51, Paris, France.
International Preliminary Report on Patentability dated Sep. 6, 2013.

* cited by examiner

Primary Examiner — Sikarl Witherspoon
(74) Attorney, Agent, or Firm — Michael W. Ferrell

(57) ABSTRACT

The invention relates to a continuous method for carrying out a multiphase aldol condensation reaction to obtain mixed α,β-unsaturated aldehydes by reacting a mixture of two aliphatic aldehydes having different numbers of carbon atoms, i.e. 2 to 5, in the molecule in a vertical tubular reactor in a concurrent flow in the presence of an aqueous solution of a basically reacting compound. In said method, the aldehyde mixture is dispersed in the aqueous phase in the form of drops, and the aqueous solution of the basically reacting compound flows through the tubular reactor as a continuous phase in laminar conditions.

17 Claims, 2 Drawing Sheets

METHOD FOR CARRYING OUT MULTIPHASE ALDOL CONDENSATION REACTIONS TO GIVE MIXED α, β-UNSATURATED ALDEHYDES

CLAIM FOR PRIORITY

This application is a national phase application of PCT/EP2012/000523 FILED Feb. 9, 2012 which was based on application DE 10 2011 012 846.8 filed Mar. 3, 2011. The priorities of PCT/EP2012/000523 and DE 2011 012 846.8 are hereby claimed and their disclosures incorporated herein by reference.

TECHNICAL FIELD

The present invention relates to a process for performing polyphasic aldol condensation reactions to give mixed α,β-unsaturated aldehydes in a tubular reactor under laminar conditions.

BACKGROUND

The aldol condensation reaction of saturated aldehydes with elimination of water to give the corresponding unsaturated dimer or α,β-unsaturated aldehyde is a reaction which is familiar in organic chemistry. The conversion can be effected with only one particular aldehyde compound in a self-condensation reaction, or else between aldehydes with a different number of carbon atoms in a mixed aldol condensation reaction. In order that the addition of two aldehyde molecules to give the β-hydroxyaldehyde can be followed by the intramolecular elimination of water and hence the formation of the α,β-unsaturated bond, at least one α-aldehyde bearing two hydrogen atoms on the α-carbon atom to the carbonyl group must be present in the aldol condensation reaction.

The deliberate suppression of the elimination of water from the β-hydroxyaldehyde intermediate is, if anything, restricted to special cases. According to WO 95/07254 A1, the aldol addition of n-butyraldehyde is performed with aqueous sodium hydroxide solution in the presence of polyethylene glycol at low temperatures. After neutralization of the basic catalyst and removal of the aqueous phase, the organic phase comprising 2-ethyl-3-hydroxyhexanal is hydrogenated. The target product desired is 2-ethyl-1,3-hexanediol, and the formation of 2-ethylhexanol is to be suppressed as far as possible.

Of greater industrial significance, however, is the preparation of 2-ethylhexanol by the aldol condensation reaction. The alcohol is prepared proceeding from n-butyraldehyde in the presence of an alkaline catalyst, typically an aqueous sodium hydroxide solution, at elevated temperature via the 2-ethylhexenal intermediate formed with elimination of water. The α,β-unsaturated aldehyde is subsequently hydrogenated to give 2-ethylhexanol, typically in the gas phase in a first stage with a subsequent liquid phase hydrogenation in the second stage (EP 0 420 035 A1). The water of reaction released dilutes the aqueous sodium hydroxide solution, which is likewise contaminated with organic impurities such as butyrates. Therefore, a portion of the diluted and contaminated aqueous sodium hydroxide solution constantly has to be discharged and replaced by fresh alkali. The aldol condensation of n-butyraldehyde in the presence of an aqueous sodium hydroxide solution can be performed, for example, in a stirred tank as described in U.S. Pat. No. 3,763,247 or DE 927 626, or in a packed column operated in countercurrent [G. Dümbgen, D. Neubauer, Chemie-Ing.-Tech. 41, 974 (1969)].

However, reaction in a stirred tank is disadvantageous since, in this type of reaction design, heat removal can be problematic and the operation of mechanically moving parts requires intensive maintenance and frequent repairs.

It is also known that n-butyraldehyde and aqueous sodium hydroxide solution can be mixed vigorously in a mixing pump, and the heterogeneous mixture can be left in the turbulent state after leaving the mixing pump. According to U.S. Pat. No. 2,468,710, the mixture is conducted through a mixing zone and then passed, for completion of the reaction, into a reaction vessel from which the desired aldol condensation product is removed at the top, and from which a liquid stream is recycled via a bottom draw. According to GB 761,203, the heterogeneous mixture is conducted through a flow tube in a turbulent manner by means of the mixing pump, and then introduced into a phase separator. The lighter organic phase is removed, while the aqueous sodium hydroxide solution is partly discharged and partly recycled back into the aldol condensation process. The known process can also be applied to the mixed aldol condensation reaction of different aldehydes, for example to the reaction of acetaldehyde with n-butyraldehyde, which leads to a mixture of α,β-unsaturated aldehydes in which the compounds from the self-aldolization and mixed aldolization are present.

EP 1 106 596 A2 concerns the performance of the aldol condensation reaction in a tubular reactor. The known process is characterized by the specification of a load factor which is the minimum that should be established to ensure the turbulent operation of the tubular reactor. A characterizing feature is the high ratio of the mass flow rate of the aqueous catalyst phase to that of the aldehyde phase, such that the aqueous catalyst phase forms the continuous phase, in which the aldehyde phase is present dispersed in fine droplets. The aqueous catalyst phase may optionally also comprise a water-soluble solvent, such as diethylene glycol, in order to facilitate mass transfer between the aqueous catalyst phase and the organic aldehyde phase. By way of example, the aldol self-condensation of n-pentanal or 3-methylbutanal is discussed, as is the aldol condensation of an aldehyde mixture composed of n-pentanal and 2-methylbutanal.

The aldol condensation of aliphatic pentanals to give α,β-unsaturated $C_{10}$-aldehydes is likewise described in WO 2010/105892 A1. In this process too, a tubular reactor is employed, the organic phase being dispersed in the aqueous catalyst phase in the form of droplets. The average Sauter diameter of the droplets is between 0.2 and 2 mm. This droplet size can be established with a low energy input and at the same time ensures high mass transfer between the dispersed organic phase and the continuous aqueous catalyst phase.

The known processes for performing the aldol condensation to give α,β-unsaturated aldehydes require a high energy input to operate a flow tube or a tubular reactor in the turbulent state. The prior art either proposes the use of mixing pumps with a downstream flow tube or recommends, in the case of a tubular reactor, a high ratio of the mass flow rates of the aqueous catalyst solution to the aldehyde phase supplied. A disadvantage in this process is, however, the use of a very high mass flow rate of aqueous catalyst solution, such that only a small amount of organic product is conducted through the reactor per unit time and volume. If a water-soluble solvent is used in addition, the purification complexity increases for the desired product. In the case of use of interface-active substances too, increased contamination of the aldolization wastewater discharged with organic impurities is to be expected. The operation of mixing pumps is energy-intensive and increases the maintenance expenditure. The aldol condensation reaction of higher aldehydes, such as $C_5$-aldehydes and higher, likewise requires a comparatively high reaction temperature in order to achieve very substantial elimination of water from the β-hydroxyaldehyde intermediate to give the α,β-unsaturated aldehyde. If the desired target product is to result from the mixed aldolization of two different aldehydes, the reaction conditions should be adjusted such that the self-condensation of the respective starting aldehydes is reduced to a very minor level.

It is therefore an object of the present invention to provide a process for performing polyphasic aldol condensation reactions to give mixed α,β-unsaturated aldehydes, which requires a low level of technical complexity and is of low energy intensity, and which features a high space-time yield of mixed aldol condensation products or α,α-unsaturated aldehydes. In addition, the risk potential attendant to working with lower aldehydes which are of marked volatility and have a low ignition temperature is to be minimized. The mixed aldol condensation products are likewise to be obtained with high conversion and high selectivity, and the formation of α,β-unsaturated aldehydes from the self-condensation and formation of by-products, more particularly the formation of high-boiling condensation products, is to be suppressed.

SUMMARY OF INVENTION

The present invention therefore provides a continuous process for performing a polyphasic aldol condensation reaction to give mixed α,β-unsaturated aldehydes in a tubular reactor by reaction of two aliphatic aldehydes which have different carbon numbers and contain 2 to 5 carbon atoms in the molecule. The process is characterized in that the aliphatic aldehydes are mixed separately in a molar ratio of 1:1 to 5:1, then the aldehyde mixture and an aqueous solution of a basic compound are introduced via the base into an upright tubular reactor in cocurrent, the aqueous solution of the basic compound forming the continuous phase which flows through the tubular reactor under laminar conditions, and the aldehyde mixture forming the phase dispersed in droplet form in the continuous phase and the aldehyde condensation reaction being performed at a temperature up to 90° C. and the tubular reactor being operated with a space velocity V/Vh of the aldehyde mixture per unit reactor volume and time of 0.1 to 1.3.

BRIEF DESCRIPTION OF DRAWINGS

The invention is described in detail below with reference to the drawing wherein.

DETAILED DESCRIPTION

Figure 1:
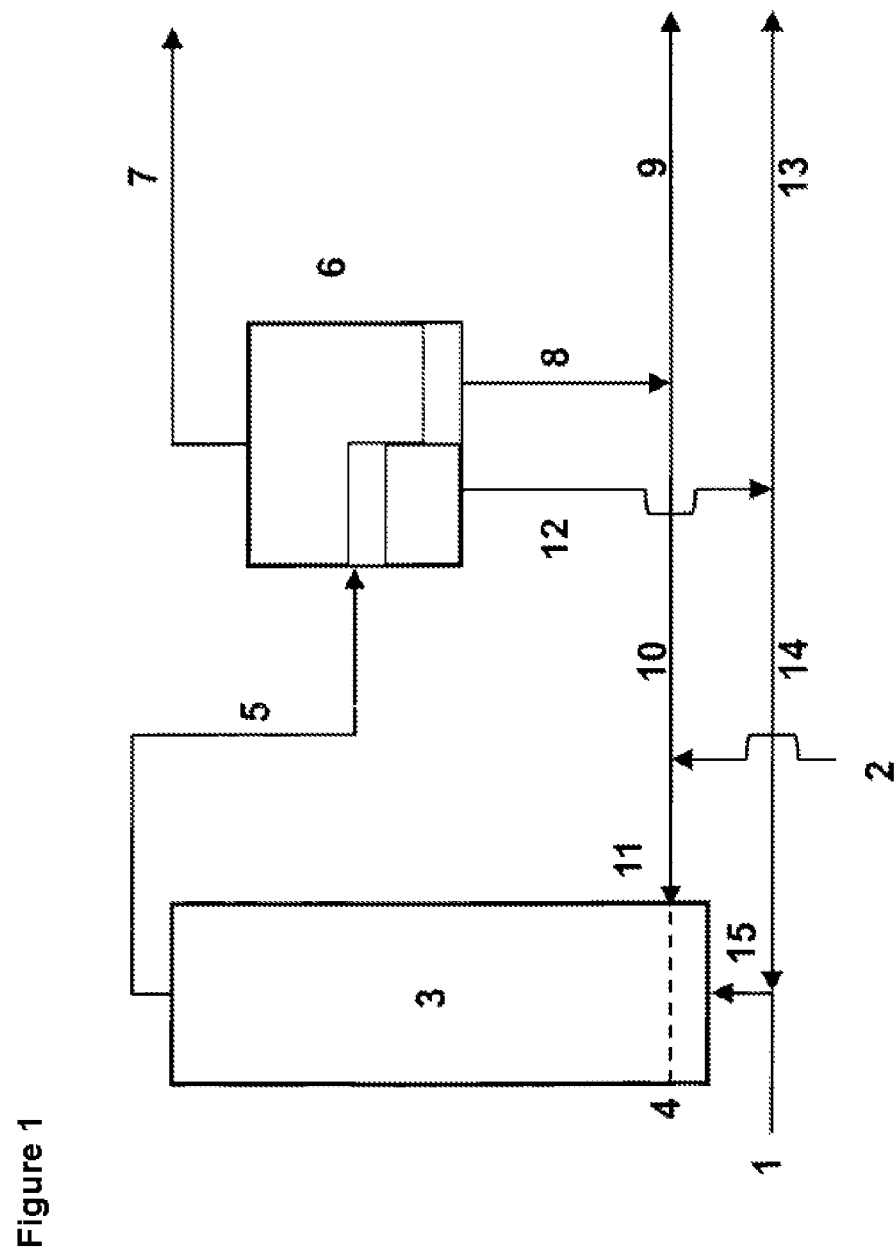
FIG. 1 is a schematic diagram illustrating operation of the inventive process for manufacturing mixed α,β-unsaturated aldehydes in a first embodiment.

The invention is described in detail below in connection with the Figures for purposes of illustration, only. The invention is defined in the appended claims. Terminology used throughout the specification and claims herein are given their ordinary meanings, unless otherwise specifically indicated.

The term "mixed α,β-unsaturated aldehydes" in the context of the invention is understood to mean the products which are formed by the aldol condensation reaction of two aldehydes with different carbon numbers. In order that the elimination of water can proceed from the β-hydroxyaldehyde formed as an intermediate, at least one aldehyde component in the aldehyde mixture must bear two hydrogen atoms on the α-carbon atom adjacent to the carbonyl group. The two aliphatic aldehydes are first premixed in a separate apparatus before entry into the tubular reactor and are then supplied as a mixture to the tubular reactor.

This blending can be effected, for example, in an upstream stirred vessel. According to the boiling point situation of the aliphatic aldehydes used, it may be advisable to perform the upstream mixing operation with cooling or under autogenous pressure in closed vessels.

The organic phase and the aqueous phase are completely immiscible or are only of very low miscibility with one another, and form a polyphasic liquid mixture in the upright tubular reactor, in which the organic phase forms the dispersed phase, and the aqueous phase comprising the basic compound or the aldolization catalyst is the continuous phase. For the continuous phase, the flow characteristics in the tubular reactor downstream of the base region in which the streams enter the tubular reactor can be described as laminar flow characteristics.

In order to ensure the laminar flow state of the continuous or aqueous, catalyst-containing phase in the tubular reactor, the mass flow rate, the substance values of density and dynamic viscosity of the continuous phase, and the hydraulic internal diameter of the tubular reactor should be in such a relation that the characteristic Reynolds number which indicates the transition from the laminar state to the turbulent state is not exceeded. The formula relationship for calculation of the Reynolds number according to equation 1:

$$Re = w\rho d/\eta \tag{1}$$

where w=mass flow rate [kg/h] of the continuous phase, $\rho$=density [kg/m$^3$] of the continuous phase, d=hydraulic internal diameter of the tubular reactor [m] and $\eta$=dynamic viscosity [Pa*s] of the continuous phase is common knowledge (VDI Wärmeatlas, 7$^{th}$ edition 1994, Lbl, eq. (2); Grundlagen der Einphasen- and Mehrphasenströmungen [Fundamentals of monophasic and polyphasic flows], Heinz Brauer, Verlag Sauerländer, Aarau and Frankfurt am Main, 1971). The critical Reynolds number is reported to be 2320. Below this number, a laminar flow state is present.

Since reactor internals such as static mixers or column packings increase the turbulence in the tubular reactor, the use thereof is not very advisable. However, the use thereof is not ruled out provided that the mass flow rate of the continuous phase for a given hydraulic internal diameter is adjusted such that the continuous phase flows through the upright tubular reactor under laminar conditions. In contrast, cooling coils or cooling fingers for removal of the heat of reaction may be installed in the tubular reactor, the continuous phase flowing past them without disruption of the laminar state.

In one embodiment of the process according to the invention, the organic, aldehyde-containing phase and the aqueous, catalyst-containing phase are fed separately but simultaneously into the base region of the tubular reactor. In the base region, it is possible to provide internals which ensure dropletized distribution of the entering aldehyde-containing phase in the aqueous, catalyst-containing solution. The internals installed may, for example, be nozzles, porous sinter plates or lances, through which the aldehyde-containing phase enters the tubular reactor flooded with the aqueous, catalyst-containing phase. In the reactor region below these internals, there is still a residual volume into which the aqueous, catalyst-containing phase flows. In the reactor region above the internals for supply of the aldehyde-containing phase, preferably no further mixing elements are installed. Cooling devices for heat removal can, however, be provided without disrupting the flow characteristics of the continuous phase.

Even though there may be turbulent zones at the base of the tubular reactor in the inflow region of the two liquid streams, the flow characteristics of the continuous phase change to a laminar state over the length of the tubular reactor downstream of the base region. The upright tubular reactor is flooded with the continuous phase, in which the aldehyde-containing, organic phase is dispersed in droplet form after it enters the base region. The organic, aldehyde-containing droplets flow as a result of their relatively low density from the entry point in the base region of the tubular reactor in the direction of the top of the reactor.

Due to the difference in density, the rate of ascent of the dispersed organic droplets in the tubular reactor is greater than that of the continuous aqueous phase.

The movement characteristics of these dispersed droplets in the continuous phase can be derived from commonly known flow relationships (VDI-Wärmeatlas, 10$^{th}$ edition 2006, Lda 8, 9 and 14). For description of the buoyancy forces, what is called the Archimedes number has been found to be appropriate:

$$A_r = \frac{d_p^3 \cdot g \cdot \rho_K \cdot \Delta\rho}{\eta_K^2} \quad (2)$$

In this formula, $d_p$[m] is the diameter of the droplet of the dispersed organic phase, g [m/s$^2$] the acceleration due to gravity, $\rho_K$ [kg/m$^3$] the density of the continuous phase, $\Delta\rho$ [kg/m$^3$] the density difference between the continuous and dispersed phases, and $\eta_K$ [Pa.s] the dynamic viscosity of the continuous phase. The Archimedes number can be used to conclude the relative velocity, the droplet ascent and hence the relative velocity of the disperse phase in the continuous phase being low in the case of a small Archimedes number.

For the range of very small droplets, droplets with a rigid phase boundary can be assumed, such that the droplets rise constantly in a stable manner through the continuous phase in the direction of the top of the reactor. This region of the rigid phase boundary is described in numerical terms by:

$$A_r \leq 1.83 \cdot K_{F,\Delta\rho}^{0.275} \quad (3)$$

where $K_{F, \Delta\rho}$ is the modified liquid characteristic where $$K_{F,\Delta\rho} = \frac{\rho_K \cdot \sigma^3}{g \cdot \eta_K} \cdot \frac{\rho_K}{\Delta\rho} \quad (4)$$

in which σ [N/m] represents the surface tension and the rest of the formula symbols are as defined in equation (2).

When the droplet size and hence the droplet velocity increases, the Archimedes number becomes greater than the limiting value calculated according to equation (3), and there is at first movement of the phase interface of the droplet, which causes internal circulation within the droplet. With a further increase in the droplet diameter, there is oscillation with deformation of the droplet until it falls apart into smaller fragments. The stability of the droplet of the dispersed phase can be estimated according to equation (5).

$$\frac{We_D}{Fr} \cdot \frac{\Delta\rho}{\rho_D} > 9 \quad (5)$$

In this equation, $We_D$ means the Weber number of the dispersed phase and Fr the Froude number. These dimensionless characteristics can be calculated according to VDI-Wärmeatlas, 10$^{th}$ edition 2006, Lda 14 from the substance data. $\rho_D$ [kg/m$^3$] is the density of the dispersed phase and $\Delta\rho$ [kg/m$^3$] the density difference between the continuous and the dispersed phase. When the limiting value specified in equation (5) is exceeded, the probability of sufficient stability of the droplet becomes very low.

For the operation of the tubular reactor by the process according to the invention, the conditions according to equations (3) and (5), more particularly the droplet size of the dispersed phase, should be adjusted such that stable droplets with a rigid phase boundary can be assumed, and the relative velocity of the dispersed organic phase relative to the continuous phase is comparatively low. The smaller the droplet diameter, the greater the exchange area.

For the further configuration of the process according to the invention, the aldehyde mixture made up and the aqueous, catalyst-containing phase can be dispersed in a static mixing element upstream of the tubular reactor, and then introduced to the base of the tubular reactor flooded with the continuous phase. Such static mixers are supplied commercially, for example, as Sulzer or Kenicks mixers with specific product lines for the dispersion of low-viscosity liquids. In this embodiment of the process according to the invention, the dispersed liquid mixture is produced outside the tubular reactor and then introduced into the tubular reactor.

The residence time in the upstream mixing element is only short, such that the organic aldehyde mixture is dispersed in droplet form in the aqueous catalyst phase, but the aldol addition and condensation reaction sets in only to a minor degree. Only after entry of the polyphasic liquid mixture into the upright tubular reactor does the conversion to the α,β-unsaturated aldehydes set in to a significant degree.

Additional internals at the reactor base are not absolutely necessary, but are not ruled out either, provided that a laminar flow state of the continuous phase over the reactor length is ensured.

In the case of use of an upstream static mixing element, the droplet diameter of the dispersed liquid droplets can be determined experimentally by means of the Weber and Reynolds numbers according to Streiff F.; Recent Prog. Genie Proc. 11. No. 51 (1997) page 307. In general, the droplet diameter for static mixers is also reported by the manufacturer.

At the top of the reactor, the polyphasic liquid mixture is drawn off and passed into a phase separator or settling vessel in which the heavier aqueous solution of the basic compound separates. The water of reaction formed in the aldol condensation dilutes this aqueous solution. Likewise present are water-soluble organic compounds, such as carboxylates formed by aldehyde oxidation, and organic constituents due to incomplete phase separation. A portion of the contaminated aqueous phase is therefore discharged.

The undischarged aqueous phase is recycled as a catalyst circulation stream, supplemented with fresh alkali comprising the basic compound as an aldolization catalyst, and introduced to the base of the upright tubular reactor.

The organic phase removed, which comprises starting aldehydes, the mixed α,β-unsaturated aldol condensation product and the α,β-unsaturated aldol condensation products formed by self-addition of one aldehyde type, and higher-boiling by-products, can be separated in downstream purification steps and then processed further, for example via full hydrogenation to alcohols, or via partial hydrogenation to give the saturated aldehyde, which can subsequently be oxidized to the corresponding carboxylic acid. It is likewise possible to remove a substream of the organic phase and return it back to the tubular reactor as a liquid circulation stream, in order to achieve full conversion of the starting aldehydes if the content of the starting aldehydes in the organic phase of the reactor output is still too high in straight pass.

The aqueous solution contains a basic compound as a catalyst for the aldol condensation reaction. Suitable basic compounds are hydroxides, carbonates, hydrogencarbonates or carboxylates of the alkali metals and alkaline earth metals, including in the form of mixtures thereof. Preference is given to using alkali metal hydroxides such as sodium hydroxide. The concentration of the basic compound is generally 0.1 to 15% by weight, preferably 0.1 to 5% by weight, based on the aqueous solution. The aqueous catalyst solution is used in such an amount that from 10 to 140 and preferably from 20 to 60 parts by weight of basic compound, calculated as the pure substance, are used per 100 parts by weight of aldehyde mixture.

For the mixed aldol condensation reaction to give $\alpha,\beta$-unsaturated aldehydes, a mixture of two aliphatic aldehydes of different carbon numbers with 2 to 5 carbon atoms in the molecule is used, though at least one type of aldehyde must bear two hydrogen atoms on the $\alpha$-carbon atom adjacent to the carbonyl function in order that there is elimination of water after the addition step. Examples of aliphatic aldehydes with two hydrogen atoms in the $\alpha$-position are acetaldehyde, propionaldehyde, n-butyraldehyde, n-pentanal or 3-methylbutanal.

Examples of aliphatic aldehydes with a hydrogen atom on the $\alpha$-carbon atom are isobutyraldehyde or 2-methyl-butanal.

The two aliphatic aldehydes with the different carbon numbers are blended in a molar ratio of 1:1 to 5:1, preferably of 1:1 to 3:1, and converted by the process according to the invention to the mixed $\alpha,\beta$-unsaturated aldol condensation product. The process according to the invention is particularly suitable for the mixed aldolization of acetaldehyde with n-butyraldehyde to give 2-ethylbutenal, of acetaldehyde with propionaldehyde to give 2-methylbutenal, of acetaldehyde with n-pentanal to give 2-ethylpentenal, of propionaldehyde with n-butyraldehyde to give 2-ethylpentenal and 2-methylhexenal, of propionaldehyde with n-pentanal to give 2-methylheptenal and 2-propylpentenal, or of n-butyraldehyde with n-pentanal to give 2-ethylheptenal and 2-propylhexenal. The aldehydes used may, as well as the respective main component, also contain small amounts of preparation-related impurities. For example, n-butyraldehyde may still contain small amounts of isobutyraldehyde if n-butyraldehyde is prepared via propylene hydroformylation. In the same way, n-pentanal, which is obtainable via butene-1 hydroformylation, may also have small amounts of 2-methylbutanal.

The formation of the mixed $\alpha,\beta$-unsaturated aldol condensation product from the self-condensation of one type of aldehyde, for example the formation of crotonaldehyde and 2-ethylhexenal in the mixed aldolization of acetaldehyde with n-butyraldehyde, reduces the yield of the mixed $\alpha,\beta$-unsaturated aldol condensation product, but these products can be marketed, for example, as alcohols after complete hydrogenation. In order, however, to reduce the occurrence of high-boiling by-products which are not products of value, the aldol condensation reaction is performed at temperatures up to 90° C., preferably in the range from 10° C. to 65° C. and especially in the range from 30° C. to 60° C. The reaction is conducted under autogenous pressure or slightly elevated pressure, although the employment of higher pressures, for example up to 0.8 MPa, is not ruled out.

In continuous mode, the tubular reactor is operated at a reactor space velocity V/Vh of the aldehyde mixture per unit reactor volume and time of 0.1 to 1.3, preferably of 0.8 to 1.3. A higher reactor space velocity of the aldehyde mixture should be avoided because the aldol condensation reaction then does not proceed to completion and the organic phase removed has too high a residual content of the starting aldehydes. In the case of excessively low reactor space velocity, the plant capacity is not utilized optimally. On startup of the process performed continuously, the upright tubular reactor is first flooded with the aqueous solution of the basic compound. Subsequently, the organic, aldehyde-containing liquid stream and the aqueous solution of the basic compound are fed in via the base of the tubular reactor. The organic and aqueous streams can be supplied separately but simultaneously via the base of the tubular reactor, such that the organic/aqueous polyphasic system is formed within the tubular reactor. It is likewise possible to mix the organic and aqueous streams in a static mixing element upstream of the tubular reactor, such that the organic/aqueous polyphasic system is introduced into the tubular reactor at the base.

The operation of the tubular reactor in cocurrent with the continuous phase under laminar conditions allows, based on the mass flow rate of the aqueous phase, a comparatively high mass flow rate of the organic phase through the reactor. In general, the ratio of the mass flow rate of the aldehyde mixture to that of the aqueous solution of the basic compound is in the range of 1 to (5-56), preferably 1 to (10-32). The comparatively high proportion of organic product in the tubular reactor distinctly improves the plant efficiency. The operation of the tubular reactor also enables a simple, energy-efficient reaction regime without the use of complex mixing pumps and maintenance-intensive mechanical plant parts, and also complex column internals, for example static mixers installed into the tubular reactor.

As a result of the dilution of the aldehydes used with the aqueous solution of the basic compound, this reaction regime also allows homogeneous removal of heat and avoids the formation of temperature peaks with uncontrolled excessive reactions, such that the mixed aldol condensation reaction of the aliphatic aldehydes can be controlled very efficiently for safety purposes and proceeds very selectively to give the desired mixed $\alpha,\beta$-unsaturated aldehydes. The formation of high-boiling by-products can therefore be suppressed.

The process according to the invention is illustrated in detail hereinafter by the box diagram according to FIG. 1. The process according to the invention is, however, not restricted to the embodiment shown in the drawing. The separate blending of the two aliphatic aldehydes is not shown.

A fresh aqueous solution of a basic compound is conducted in via line (1), and fresh aldehyde mixture via line (2), and, after mixing with the respective circulation streams, introduced at the base of the tubular reactor (3), in which are installed devices (4) at the base, through which the incoming organic solution is divided into liquid droplets which flow distributed in the aqueous phase in the direction of the top of the reactor. For heat removal, cooling coils or cooling fingers may be installed in the tubular reactor (3), but these do not disrupt the laminar flow characteristics of the continuous phase (not shown in FIG. 1). At the top of the reactor, the liquid reactor output is removed via line (5) and passed into a settling vessel (6) in which the lighter organic phase separates from the heavier aqueous phase. Gaseous components are removed via line (7). The settled organic phase which contains the mixed α,β-unsaturated aldol condensation product, unconverted aldehydes and α,β-unsaturated aldol condensation products from the self-addition leaves the settling vessel (6) via line (8). A substream is discharged via line (9), which is separated in downstream distillation apparatuses into the different organic constituents (not shown in FIG. 1). The other substream is recycled as a circulation stream via line (10) and combined with fresh aldehyde mixture supplied via line (2), and fed into the reactor (3) at the base via line (11). The aqueous solution of the basic compound obtained in the settling vessel (6) flows out via line (12) and is partly removed via line (13). The other substream flows back via line (14) as a catalyst circulation stream, is combined with fresh aqueous solution of the basic compound supplied via line (1), and is pumped into the reactor (3) at the base via line (15).

Figure 2:
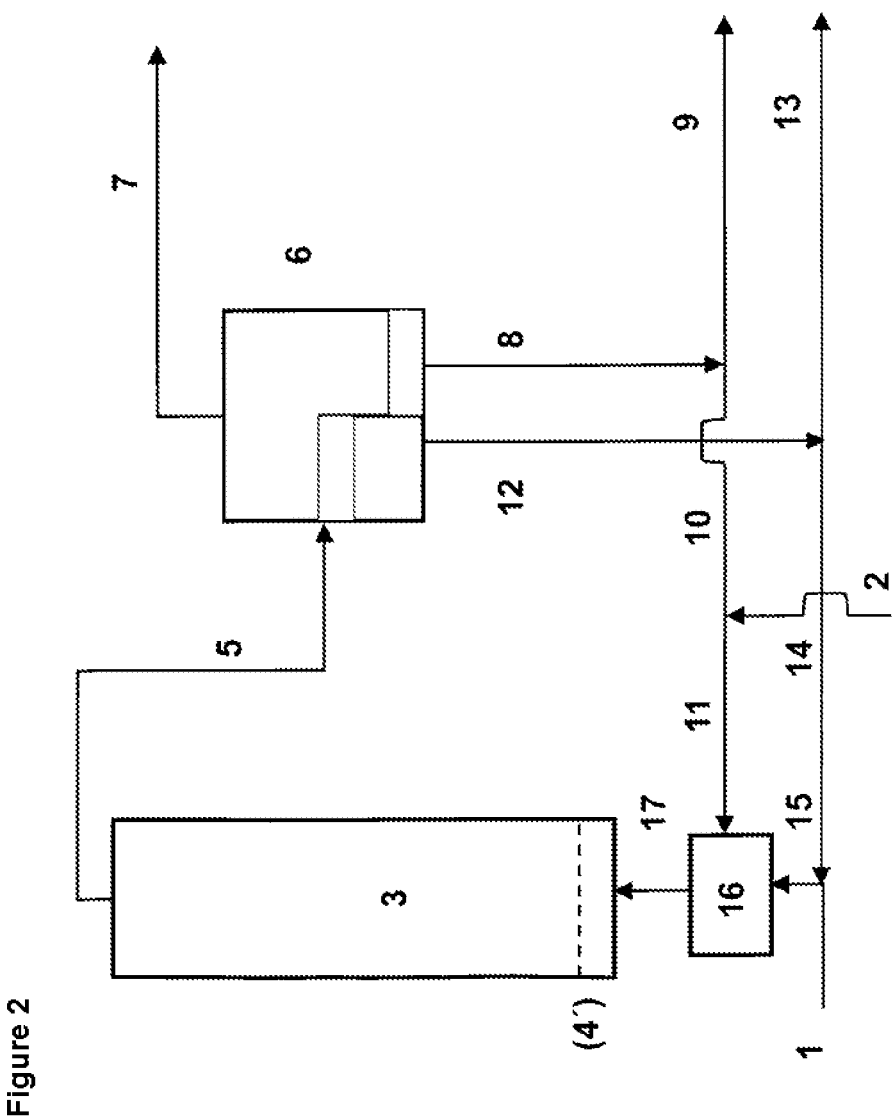
FIG. 2 is a schematic diagram illustrating operation of the inventive process for manufacturing mixed α,β-unsaturated aldehydes in a second embodiment provided with a static mixer.

The next figure, FIG. 2, shows a further embodiment of the process according to the invention using a static mixer connected upstream of the tubular reactor. The aqueous solution conducted in via line (15) and the organic solution conducted in via line (11) are dispersed in the static mixer (16). The liquid polyphasic system then enters at the base of the tubular reactor (3) via line (17). In this embodiment, it is possible to dispense with the internals (4') indicated schematically, although apparatuses in the base region of the tubular reactor are not ruled out, provided that laminar flow characteristics of the continuous phase over the length of the tubular reactor are ensured.

The process according to the invention is illustrated in detail hereinafter with reference to a few examples, but is not restricted to the embodiments described.

Experimental Setup

A tubular reactor with a capacity of 0.19 liter was first flooded with aqueous sodium hydroxide solution having a concentration of 2.5% by weight. Via the reactor base, the mixture of two aliphatic aldehydes with different carbon numbers and 2.5% by weight aqueous sodium hydroxide solution were subsequently introduced continuously into the tubular reactor. If no static mixer was employed, the two streams were conducted separately but simultaneously to the base of the tubular reactor. In the experiments with a static mixer, a Sulzer SMX DN4 mixer was used. The mixing element was mounted upstream of the reactor base, outside the tubular reactor. The organic and aqueous solutions were mixed with one another therein and then the liquid polyphasic system with the dispersed organic phase was introduced to the tubular reactor. In both embodiments, the dispersed organic phase flowed through the continuous aqueous phase in droplet form.

At the top of the reactor, the polyphasic reaction mixture was withdrawn and conducted into a settling vessel. From the separated liquid phases, both an aqueous circulation stream and an organic circulation stream were recycled back into the tubular reactor. The unrecycled aqueous phase was discharged, while the unrecycled organic phase was analyzed by gas chromatography for its content of product of value.

The reaction conditions, the continuous supply of the feedstocks and the circulation flow rates were adjusted according to the conditions in Table 1 below. Table 1 likewise reports the composition of the organic product, determined by gas chromatography in anhydrous form (in %). The experiments were conducted at a slightly elevated pressure of 0.02 MPa.

EXAMPLES 1-4

TABLE 1

Preparation of 2-ethylbutenal by mixed aldolization of acetaldehyde with n-butyraldehyde

| | Examples | | | |
|---|---|---|---|---|
| | 1 | 2 | 3 | 4 |
| Temperature [° C.] | 40 | 40 | 40 | 57 |
| Acetaldehyde [g/h] | 25 | 25 | 25 | 25 |
| n-Butanal [g/h] | 100 | 100 | 100 | 100 |
| Catalyst circulation stream [kg/h], aqueous NaOH | 1 | 1 | 4 | 1 |
| Alkali | | | | |
| Fresh NaOH (2.5% by weight) [mL/h] | 18 | 18 | 15 | 15 |
| n-Butanal/acetaldehyde (molar) | 2.5 | 2.5 | 2.5 | 2.5 |
| Sulzer mixer | without | with | with | with |
| Analysis [GC %] | | | | |
| First runnings | 0.1 | 0.1 | 0.1 | 0.1 |
| n-Butanal | 14.5 | 9.3 | 5.6 | 4.4 |
| Crotonaldehyde + intermediate runnings | 0.3 | 0.4 | 0.4 | 0.2 |
| 2-Ethylbutenal | 20.4 | 26.3 | 26.7 | 25.3 |
| Intermediate runnings | 2.6 | 3.4 | 3.0 | 2.7 |
| 2-Ethyl-2-hexenal | 32.5 | 35.2 | 35.6 | 39.2 |
| Final runnings | 29.6 | 25.3 | 28.6 | 28.1 |
| Yield of 2-ethylbutenal, based on acetaldehyde used | 41 | 55 | 53 | 49 |

For Example 3, the hydraulic data in relation to the superficial velocity of the tubular reactor are compiled in Table 2. The input mass flow rate into the tubular reactor for Example 3 is $m_x = 4.140$ kg/h, which is composed of the input of acetaldehyde and n-butanal and of catalyst circulation stream and fresh NaOH.

TABLE 2

Hydraulic characteristics based on the aqueous continuous phase; illustrative for Example 3

| | |
|---|---|
| Density ρ [kg/m$^3$] | 990 |
| Dynamic viscosity η [Pa * s] | 0.000677 |
| Hydraulic internal diameter of the tubular reactor [m] | 0.009 |
| Mass flow rate of the reactants [kg/h] | 4.140 |

Using equation (1), a Reynolds number of 239 is calculated from these characteristics. Since a lower input mass flow rate has been employed in Examples 1, 2 and 4, an even smaller Reynolds number follows according to equation (1). In Examples 1-4, stable laminar flow conditions are thus present in the continuous phase.

Due to the density difference, the rate of ascent of the dispersed phase in the tubular reactor is greater than that of the continuous phase. For Example 3, the following hydraulic characteristics for the dispersed phase are calculated using the formula relationships described in VDI-Wärmeatlas, 10$^{th}$ edition 2006, Lda 8, Lda 9 and Lda 14.

TABLE 3

Hydraulic characteristics based on the
organic dispersed phase; illustrative for
Example 3

| | |
|---|---|
| Aqueous/organic density difference [kg/m³] | 209.00 |
| Droplet diameter* [m] | 0.0008 |
| Organic/aqueous relative velocity [m/s] | 0.096 |
| Reynolds number | 106 |
| Archimedes number | 1908 |
| Weber number | 0.08 |
| Froude number | 1.24 |
| Consistency factor $K_{F,\Delta\rho}$ | $6.46 \cdot 10^{11}$ |

*manufacturer data

Using equation (5), a stability value of 0.02 is calculated, and so the forces active during flow do not lead to disintegration of the droplets. The condition in equation (2) is likewise met, and so the organic droplets ascending in the continuous phase can be described as stable droplets with a rigid phase boundary. In an analogous manner, the hydraulic characteristics for the organic dispersed phase can be calculated for Examples 1, 2 and 4, and thus the droplet stabilities can be estimated.

Examples 5-7 (mixed aldolization of n-butyraldehyde with n-pentanal) and Examples 8 and 9 (mixed aldolization of acetaldehyde and n-pentanal)

For the performance of Examples 5-7 and 8 and 9, the experimental setup used in Examples 1-4 was used.

The reaction conditions, the continuous supply of the feedstocks and the circulation flow rates were established according to the conditions in Tables 4 and 5 below. Tables 4 and 5 likewise report the composition of the organic product determined by gas chromatography, in anhydrous form (in %). In all experiments, a Sulzer SMX DN4 mixer was used, which was installed upstream of the reactor base, outside the tubular reactor. The experiments were conducted at a slightly elevated pressure of 0.02 MPa.

EXAMPLES 5-7

TABLE 4

Preparation of 2-propyl-2-hexenal and
2-ethyl-2-heptenal by mixed aldolization of
n-butyraldehyde with n-pentanal

| | Examples | | |
|---|---|---|---|
| | 5 | 6 | 7 |
| Temperature [° C.] | 55 | 80 | 80 |
| n-Butanal [g/h] | 55 | 78 | 84 |
| n-Pentanal [g/h] | 65 | 47 | 41 |
| Catalyst circulation stream [kg/h]; aq. NaOH Alkali | 2 | 2 | 2 |
| Fresh NaOH (2.5% by weight) [mL/h] | 15 | 15 | 15 |
| n-Butanal/n-pentanal (molar) | 1 | 2 | 2.5 |
| Analysis [GC %] | | | |
| First runnings | 0.1 | 0.1 | 0.1 |
| n-Butanal | 3.8 | 1.3 | 1.4 |
| 2-Methylbutanal | 0.1 | 0.1 | 0.1 |
| n-Butanol | 0.1 | 0.1 | 0.1 |
| n-Pentanal | 16.9 | 5.2 | 5.6 |
| Intermediate runnings | 0.3 | 0.4 | 0.4 |
| 2-Ethyl-2-hexenal | 21.6 | 40.8 | 47.9 |
| Intermediate runnings | 0.1 | 0.2 | 0.2 |
| 2-Propyl-2-hexenal | 13.5 | 15.7 | 13.9 |
| 2-Ethyl-2-heptenal | 13.0 | 17.0 | 15.1 |

TABLE 4-continued

Preparation of 2-propyl-2-hexenal and
2-ethyl-2-heptenal by mixed aldolization of
n-butyraldehyde with n-pentanal

| | Examples | | |
|---|---|---|---|
| | 5 | 6 | 7 |
| Intermediate runnings | 5.7 | 3.6 | 3.3 |
| 2-Propyl-2-heptenal | 12.6 | 8.3 | 6.3 |
| Final runnings + higher boilers | 12.2 | 7.2 | 5.6 |
| Yield (%) of 2-propylhexenal and 2-ethylheptenal based on n-pentanal used | 42 | 86 | 77 |

EXAMPLES 8 and 9

TABLE 5

Preparation of 2-ethylpentenal by mixed
aldolization of acetaldehyde with n-pentanal

| | Examples | |
|---|---|---|
| | 8 | 9 |
| Temperature [° C.] | 40 | 50 |
| Acetaldehyde [g/h] | 21 | 21 |
| n-Pentanal [g/h] | 102 | 102 |
| Catalyst circulation stream [kg/h], aq. NaOH Alkali | 2 | 2 |
| Fresh NaOH (2.5% by weight) [mL/h] | 20 | 15 |
| n-Pentanal/acetaldehyde (molar) | 2.5 | 2.5 |
| Analysis [GC %] | | |
| First runnings | 0.1 | 0.1 |
| Acetaldehyde | 0.2 | 0.1 |
| 2-Butenal | 0.1 | 0.1 |
| 2-Methylbutanal | 0.1 | 0.4 |
| n-Pentanal | 26.0 | 20.3 |
| Intermediate runnings | 0.4 | 0.6 |
| 2-Ethylpentenal | 22.4 | 23.5 |
| 2-Heptenal | 1.5 | 1.9 |
| Intermediate runnings | 4.3 | 3.5 |
| 2-Propylheptenal | 15.1 | 23.4 |
| Final runnings | 29.8 | 26.1 |
| Yield of 2-ethylpentenal, based on acetaldehyde used | 54 | 55 |

The invention claimed is:

1. Continuous process for performing a polyphasic aldol condensation reaction to give mixed α,β-unsaturated aldehydes in a tubular reactor by reaction of two aliphatic aldehydes which have different carbon numbers and contain 2 to 5 carbon atoms in the molecule, characterized in that the aliphatic aldehydes are mixed separately in a molar ratio of 1:1 to 5:1, then the aldehyde mixture and an aqueous solution of a basic compound are introduced via the base into an upright tubular reactor in cocurrent mode, the aqueous solution of the basic compound forming the continuous phase which flows through the tubular reactor under laminar conditions, and the aldehyde mixture forming the phase dispersed in droplet form in the continuous phase and the aldol condensation reaction being performed at a temperature up to 90° C. and the tubular reactor being operated with a space velocity V/Vh of the aldehyde mixture per unit reactor volume and time of 0.1 to 1.3.

2. Process according to claim 1, characterized in that the aliphatic aldehydes are mixed separately in a molar ratio of 1:1 to 3:1.

3. Process according to claim 1, characterized in that the aldol condensation reaction is performed at temperatures of 10° C. to 65° C.

4. Process according to claim 1, characterized in that 10 to 140 parts by weight of basic compound are used per 100 parts by weight of aldehyde mixture, calculated as the pure substance.

5. Process according to claim 1, characterized in that the ratio of the mass flow rate of the aldehyde mixture to that of the aqueous solution of the basic compound is in the range of 1 to (5-56).

6. Process according to claim 1, characterized in that the aliphatic aldehydes used are acetaldehyde, propionaldehyde, n-butyraldehyde, isobutyraldehyde, n-pentanal, 2-methylbutanal or 3-methylbutanal.

7. Process according to claim 1, characterized in that the aldol condensation reaction is performed with acetaldehyde and n-butyraldehyde, with acetaldehyde and n-pentanal, or with n-butyraldehyde and n-pentanal.

8. Process according to claim 1, characterized in that the dispersed droplets of the aldehyde mixture in the continuous phase satisfy the condition $A_r \leq 1.83 \cdot K_{F,\Delta\rho}^{0.275}$.

9. Process according to claim 1, characterized in that the aldol condensation reaction is performed at temperatures of 30° C. to 60° C.

10. Process according to claim 1, characterized in that 20 to 60 parts by weight of basic compound are used per 100 parts by weight of aldehyde mixture, calculated as the pure substance.

11. Process according to claim 1, characterized in that the ratio of the mass flow rate of the aldehyde mixture to that of the aqueous solution of the basic compound is in the range of 1 to (10-32).

12. Continuous process for performing a polyphasic aldol condensation reaction to give mixed α,β-unsaturated aldehydes in a tubular reactor by reaction of two different aliphatic aldehydes selected from acetaldehyde, propionaldehyde, n-butyr-aldehyde, isobutyraldehyde, n-pentanal, 2-methylbutanal or 3-methylbutanal, characterized in that the aliphatic aldehydes are mixed separately in a molar ratio of 1:1 to 3:1, then the aldehyde mixture and an aqueous solution of a basic compound are introduced via the base into an upright tubular reactor in cocurrent mode, the aqueous solution of the basic compound forming the continuous phase which flows through the tubular reactor under laminar conditions, and the aldehyde mixture forming the phase dispersed in droplet form in the continuous phase and the aldol condensation reaction being performed at a temperature up to 90° C. and the tubular reactor being operated with a space velocity V/Vh of the aldehyde mixture per unit reactor volume and time of 0.1 to 1.3.

13. Process according to claim 12, characterized in that the aldol condensation reaction is performed at temperatures of 10° C. to 65° C.

14. Process according to claim 12, characterized in that 10 to 140 parts by weight of basic compound are used per 100 parts by weight of aldehyde mixture, calculated as the pure substance.

15. Process according to claim 12, characterized in that the ratio of the mass flow rate of the aldehyde mixture to that of the aqueous solution of the basic compound is in the range of 1 to (5-56).

16. Process according to claim 12, characterized in that the aldol condensation reaction is performed with acetaldehyde and n-butyraldehyde, with acetaldehyde and n-pentanal, or with n-butyraldehyde and n-pentanal.

17. Process according to claim 12, characterized in that the dispersed droplets of the aldehyde mixture in the continuous phase satisfy the condition $A_r \leq 1.83 \cdot K_{F,\Delta\rho}^{0.275}$.

* * * * *